(12) United States Patent
Jan et al.

(10) Patent No.: US 6,403,368 B1
(45) Date of Patent: Jun. 11, 2002

(54) ON-SPOT HYDROPHILIC ENHANCED SLIDE AND PREPARATION THEREOF

(75) Inventors: Bor-Iuan Jan, Pingtung; Jia-Huey Tsao, Taoyuan; Chih-Wei Ho, Miaoli Hsien; Chao-Chi Pan, Hsinchu; Zu-Sho Chow, Hsinchu Hsien; Yao-Sung Chang, Hsinchu; Cheng-Tao Wu; Wen-Hsun Kuo, both of Tainan, all of (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 0 days.

(21) Appl. No.: 09/695,254

(22) Filed: Oct. 25, 2000

(30) Foreign Application Priority Data

Jul. 10, 2000 (TW) .......................... 89113659 A (51) Int. Cl.$^7$ .......................... C12M 1/34; C12Q 1/68; C07H 21/02
(52) U.S. Cl. ............... 435/287.2; 435/6; 435/287.2; 536/23.1; 536/24.3; 536/24.33
(58) Field of Search ............... 435/287.2, 7.1, 435/5, 6, 183; 436/501, 94; 536/23.1, 24.3, 24.33

(56) References Cited

U.S. PATENT DOCUMENTS

| | | | | |
|---|---|---|---|---|
| 4,466,941 A | * | 8/1984 | Cerami et al. ................ 422/57 |
| 5,439,972 A | * | 8/1995 | Charles et al. ............. 525/54.1 |
| 5,474,796 A | * | 12/1995 | Brennan .................... 427/2.13 |
| 5,501,986 A | * | 3/1996 | Ward et al. ................. 436/525 |
| 5,670,322 A | * | 9/1997 | Eggers et al. .................... 435/6 |
| 5,837,860 A | | 11/1998 | Anderson et al. |
| 6,013,440 A | * | 1/2000 | Lipshutz et al. ................ 435/6 |

FOREIGN PATENT DOCUMENTS

WO    WO 98/39481    9/1998 ............ C12Q/1/68

OTHER PUBLICATIONS

Blanchard, A.P., Kaiser R.J., & Hood, L.E.; High–density ogligonucleotide arrays; Biosensors & Bioelectronics, 1996, vol. 11, No. 6/7, pp. 687–690.

* cited by examiner

Primary Examiner—Bradley L. Sisson
(74) Attorney, Agent, or Firm—Fei-Fei Chao, Ph. D.; Venable, Baetjer, Howard & Civiletti, LLp (57) ABSTRACT

The invention discloses an on-spot hydrophilic enhanced slide/microarray. The preparation method relates to a hydrophobic copolymer prepared by blending, grafting or co-polymerization of a hydrophobic material and a compound bearing functional groups such as anhydride, imide, cyclic amide, and cyclic ester, and application of the hydrophobic copolymer onto an organic or inorganic substrate. The resulting slide has the properties of on-spot hydrophilic/hydrophobic dynamic conversion, as well as on-spot hydrophilic enhancement for the preparation of high-density and high-efficiency bio-chip/microarray.

12 Claims, 8 Drawing Sheets

(8 of 8 Drawing Sheet(s) Filed in Color)

ON-SPOT HYDROPHILIC ENHANCED SLIDE AND PREPARATION THEREOF

BACKGROUND OF THE INVENTION

1. Field of the Invention

The present invention relates to an on-spot hydrophilic enhanced slide and the preparation method thereof. More particularly, it relates to a hydrophobic copolymer prepared by blending, grafting or co-polymerization of a hydrophobic material and a compound bearing functional groups such as anhydride, imide, cyclic amide, and cyclic ester, and application of the hydrophobic copolymer onto an organic or inorganic matrix to form an on-spot hydrophilic enhanced slide.

2. Description of the Related Arts

In the current bio-chip and bio-microarray technology, most of the preparation methods involve the treatment of a matrix surface with silanization, followed by the crosslinking reaction with biomaterials. In the silanization treatment, the surface of the substrate is activated based on its material, and then treated by a hydrophilic silane such as APTES. Afterwards, the crosslinking reaction is performed via a crosslinker such as glutaldehyde to immobilize biomaterials on the substrate. The shortcomings of the method include substrate dependence, long reaction time, poor homogeneity, low reaction efficiency, and the resulting low activity for the immobilized biomaterials. Moreover, the prepared covalent bonding surface is hydrophilic, which facilitates the phenomenons of crossover and contamination among spots when the hydrophilic surface is used for a high-density microarray.

U.S. Pat. No. 5,837,860 and WO 98/39481 disclose the treatment of glass or silicon wafer with hydrophobic silane such as mercapto-silane, and the immobilization of nucleic acid probes thereon. The method involves treating a substrate surface so that mercapto-groups (HS-) with hydrophobicity are covalently bonded thereon. The hydrophobic property is suitable for the immobilization of nucleic acids/ nucleotides in high density. The method, however, requires the modification of the biomaterials to bear mercapto-groups, thereby forming disulfide bonds between the modified biomaterials and matrix surface. Blanchar, A. P. et al. (Biosensors and Bioelectronics, 1996, 11(6/7): 687–690) discloses coating photoresists onto a substrate and then development using the micro-electromechanical mask to form on-spot hydrophilic spots, wherein the region outside of the spots is hydrophobic. The preparation of high-density nucleic acid probe microarrays and in situ synthesis is carried out on this treated surface.

In these prior arts, blending, grafting or co-polymerization of a hydrophobic material and a compound bearing functional groups such as anhydride, imide, cyclic amide, and cyclic ester to prepare a hydrophobic copolymer is not disclosed. Further, the application of the prepared hydrophobic copolymer onto an organic or inorganic substrate to form an on-spot hydrophilic enhanced slide is also not disclosed.

SUMMARY OF THE INVENTION

It is therefore a primary object of the present invention to provide a method for preparing an on-spot hydrophilic enhanced slide, comprising: (a) preparing a hydrophobic copolymer in a solvent to obtain a solution of hydrophobic copolymer; (b) coating said solution of hydrophobic copolymer onto a substrate (e.g. organic or inorganic substrate); and (c) removing said solvent.

Another aspect of the present invention provides an on-spot hydrophilic enhanced slide, comprising: (i) a substrate (e.g. organic or inorganic substrate); and (ii) a layer of hydrophobic functional groups formed by a hydrophobic copolymer, wherein said layer is coated onto said substrate.

Yet another aspect of the present invention provides an on-spot hydrophilic enhanced microarray, comprising: (i) a substrate (e.g. organic or inorganic substrate); (ii) a layer of hydrophobic functional groups formed by a hydrophobic copolymer, wherein said layer is coated onto said substrate; and (iii) a biologically active material, which is immobilized onto said layer of hydrophobic functional groups.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The present invention will be more fully understood and further advantages will become apparent when reference is made to the following description of the invention and the accompanying drawings in which:

FIG. 10 is a diagram showing glass substrate coated with various ratios of PSMA, wherein

FIG. 11 is a diagram showing a glass substrate coated with PSMA, wherein

DETAILED DESCRIPTION OF THE INVENTION

The present invention features a method for preparing an on-spot hydrophilic enhanced slide by (a) preparing a hydrophobic copolymer in a solvent to obtain a solution of hydrophobic copolymer; (b) coating the solution of hydrophobic copolymer onto a substrate; and (c) removing the solvent. In accordance with the method of the present invention, the hydrophobic copolymer is prepared by blending, grafting or co-polymerization of a hydrophobic material and a compound bearing functional groups (e.g. anhydride, imide, cyclic amide, or cyclic ester). The resulting hydrophobic copolymer is then coated onto an organic or inorganic substrate to form a hydrophobic layer with covalent bonding functional groups, which is useful in the preparation of a high-density microarray. In addition, the covalent bonding reaction is reduced to one-step reaction so that the immobilization efficiency can thus be improved. Further, the compound bearing functional groups (e.g. anhydride, imide, cyclic amide, and cyclic ester) or the derivatives thereof, can be blended, grafted, or co-polymerized with a hydrophobic material in various ratios to adjust the density of functional groups on the matrix surface which can be provided for covalent bonding. Moreover, another hydrophilic group will be formed when the structure of anhydride, imide, cyclic amide, or cyclic ester is attacked by a biomaterial or a modified nucleophile, which leads to the formation of on-spot hydrophilic enhancement and thus bears positive or negative charge. It is therefore beneficial to enhance not only the covalent bonding on the microarray but also the specificity of subsequently biochemical reaction, thereby improving the choke point of the traditional hydrophilic silanization.

The term "on-spot hydrophilic enhanced" used herein refers to the formation of another hydrophilic group via ring-opening when the structure of anhydride, imide, cyclic amide, or cyclic ester on the hydrophobic matrices prepared by the present invention is attacked by a nucleophile (e.g. amine modified oligonucleotide probe), which leads to the formation of on-spot hydrophilic enhancement. At this point, the hydrophobic surface is converted to hydrophilic, whereas the other region remains hydrophobic.

Another advantage of the present invention is that the negative charge (for example, anhydride group) or positive charge (for example, imide, cyclic amide) can be formed at the on-spot hydrophilic enhanced region under an appropriate condition when the ring-opening reaction occurs. This property improves the orientation of the immobilized biomaterials.

The schemes of the aforementioned reaction are shown below:

poly(styrene-co-maleic anhydride)

Unless otherwise defined, all technical and scientific terms used herein have the same meaning as commonly understood by one of ordinary skill in the art to which this invention belongs. In addition, the abbreviations throughout the specification have the following meanings: PS, polystyrene; MA, maleic anhydride; PSMA, poly(styrene-co-maleic anhydride); MI, maleimide; PSMI, poly(styrene-co-maleimide); PE, polyethylene; and PEMA, poly(ethylene-co-maleic anhydride).

According to the method for preparing an on-spot hydrophilic enhanced slide of the invention, the type of the substrate used herein is not limited, and can include an organic or inorganic substrate (i.e. substrate-independent). Organic substrates include a polymer polymerized by organic monomers. Suitable organic monomers include, for example, ethylene, styrene, propylene, ester, acrylic acid, acrylate, alkyl acrylic acid, or alkyl acrylate. Inorganic substrates include, but are not limited to silicon wafer, ceramic material, glass or metal. In one preferred embodiment, the hydrophobic copolymer prepared by the present invention (as described below) can be directly molded by injection or compression to form an on-spot hydrophilic enhanced slide with hydrophobic surface, wherein the technique of injection or compression molding is well known to those skilled in this art. Suitable hydrophobic copolymers used herein include, but are not limited to, poly(styrene-co-maleic anhydride), poly(styrene-co-maleimide), or poly(ethylene-co-maleic anhydride).

If an inorganic substrate is employed, an activation step of the substrate surface can be carried out prior to coating hydrophobic copolymers thereon to enhance the adhesion between the substrate surface and hydrophobic copolymers. The activation step includes treatment of the substrate surface with an acid or a base, or treatment of the surface by plasma activation.

According to the preparation method of the invention, the substrate surface can be cleaned prior to coating hydrophobic copolymers thereon to prevent the deposition of impurities or contaminants on the substrate surface. The cleaning step is performed by pretreatment with a solvent and/or sonication, based on the material of the substrate. Suitable solvents include, but are not limited to surfactant, water, alcohol or acetone.

In accordance with the present invention, the hydrophobic copolymer is prepared by blending, grafting or co-polymerization of a hydrophobic material and a compound bearing a functional group such as anhydride, imide, cyclic amide, or cyclic ester. The hydrophobic material can include any compound that blends, grafts or co-polymerizes with an anhydride, such as maleic anhydride, 2-decenylsuccinic anhydride, hex-2-enylsuccinic anhydride, tetrahydrophthalic anhydride; imide, such as maleimide, 4-amino-phthalimide; cyclic amide, such as 3-methyl-2-pyridone; or cyclic ester, such as 5-methylfuranone, 4-aminophthalide, tetronic acid. Such hydrophobic materials include styrene, urethane, ethylene, or derivatives thereof. In a particularly preferred embodiment of the present invention, the hydrophobic material used is polystyrene or ethylene, and the prepared hydrophobic copolymers thus include PSMA, PSMI, or PEMA.

The method for coating the hydrophobic copolymer onto a matrix is not limited, and is understood by one of ordinary skill in the art to which chemical engineering and semiconductor process belongs, to include spin coating, screen printing, roller coating, curtain coating, or dip coating, etc. In one preferred embodiment, the coating method used herein is spin coating, preferably at 3,000–6,000 rpm, and more preferably at 4,000 rpm.

After coating the hydrophobic copolymer onto a substrate, the excess solvent is removed by means of, for example, vacuum evaporation, heating evaporation, or evaporation under reduced pressure, wherein the method of heating evaporation is carried out at a temperature not higher than 100° C. to prevent the matrix from being destroyed or to prevent undesired polymerization. The preparation of the slide of the invention is accompanied after the solvent is removed.

In another aspect of the present invention, an on-spot hydrophilic enhanced microarray is provided, comprising a biologically active material, which is immobilized onto the matrix described above. The immobilization is achieved by way of contacting the bio-molecules with the on-spot hydrophilic enhanced slide of the present invention. The linkage between a nucleophile such as an amine group, which is present in the molecule (e.g. protein) itself or in a chemically-modified entity, and functional groups such as anhydride, imide, cyclic amide or cyclic ester on the matrix surface is formed via the ring-opening reaction, whereas the other side of the ring bears negative charge (e.g. anhydride group) or positive charge (e.g. imide, cyclic amide), thereby improving the orientation of the immobilized biomaterials.

Bio-molecules used as the biologically active material that are suitable for use in the invention include nucleic acid, oligonucleotide, peptide nucleic acid (PNA), antigen, antibody, enzyme, or protein. Stable amide linkages are formed after such bio-molecules are reacted with the functional groups of the on-spot hydrophilic enhanced slide of the invention. As compared with the prior arts in which the bonding is created via a two-step reaction (i.e., by the silane-based polymer and followed by adding a crosslinker such as glutaldehyde), the reaction is reduced to one-step reaction in the present invention. Thereby, the time for the immobilization reaction is substantially decreased and efficiency is increased.

Another feature of the present invention is the property of on-spot hydrophobic/hydrophilic dynamic conversion when the slide is applied to immobilization of the biomaterials. In addition, a high-density microarray can be prepared according to the matrix with a functional layer of hydrophobic characteristic, and the biomaterials' orientation during subsequent reaction can be improved by way of the on-spot hydrophilic conversion. Further, the preparation time according to the method of the invention is much less than that of the conventional method, and the homogeneity of the slide of the present invention is increased. In other words, the number of the functional groups (e.g. anhydride, imide, cyclic amide, or cyclic ester) appearing on the matrix and the bonding strength is average. Moreover, the on-spot hydrophilic enhanced microarray of the present invention can markedly decrease the time required for immobilization of biomaterials onto the matrix. In one preferred embodiment, the immobilization time is less than 40 minutes.

Without intending to limit it in any manner, the present invention will be further illustrated by the following examples.

EXAMPLE 1

Preparation of PSMI

Figure 1:
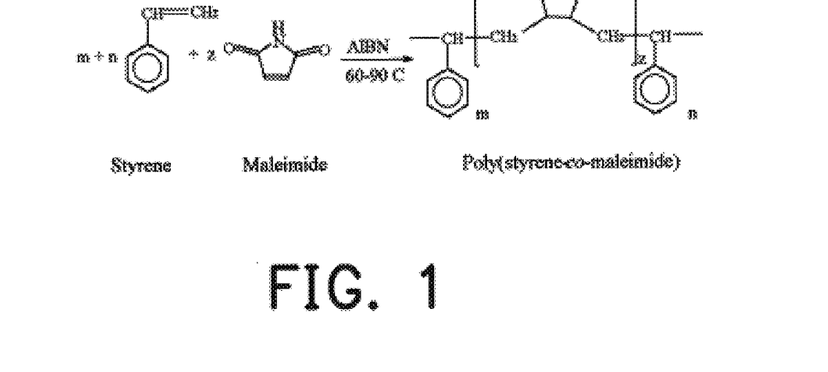
FIG. 1 is a schematic diagram showing the synthesis of PSMI.

The preparation scheme is shown in FIG. 1. To a pre-filled nitrogen or argon reaction bottle containing toluene, polystyrene and maleimide were added in a molar ratio of 4:1, followed by addition of 0.5% N,N'-azobisisobutyronitrile dropwise. The co-polymerization was conducted at 60° C. for 6 hours, and then ceased by aeration to obtain PSMI in toluene.

EXAMPLE 2

Effect of PSMA and PS on Immobilization of Oligonucleotide

Figure 2:
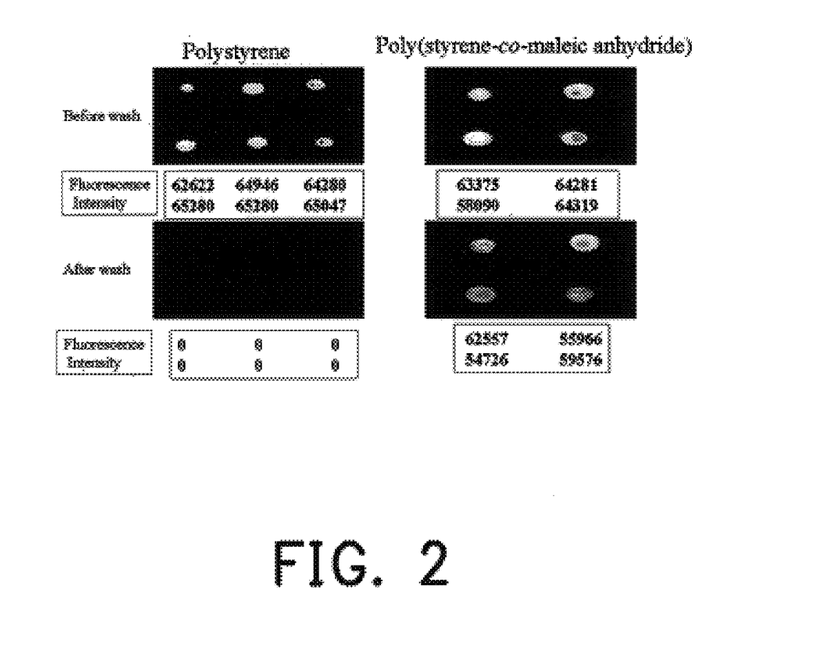
FIG. 2 is a comparative diagram showing the fluorescence intensity after immobilization of labeled oligonucleotide probe using a glass slide coated with PS and PSMA, respectively as a matrix.

PSMA (Aldrich, Cat. No. 44240–2) and PS (Aldrich, Cat. No. 43010–2) were dissolved in toluene, respectively, and then coated onto glass substrates at 4,000 rpm to form PSMA and PS slides. The slides were dried in an oven at 100° C. to remove toluene. A synthetic oligonucleotide probe Sp5 composed of 25 nucleotides in which the 5' end was labeled with fluorescence and the 3' end bore amine group, was immobilized to the aforementioned slides to perform a ring-opening reaction. The immobilization conditions were described as follows: 0.5 $\mu$M of Sp5 in 2×SSC buffer (pH 7.0) was spotted on the slides and incubated at 37° C. for 1 hour. The slides were washed with 0.2% SDS for 10 minutes. The fluorescence analyses were performed for the slides with and without washing (control) to monitor the immobilization efficiency. The result is shown in FIG. 2.

EXAMPLE 3

Effect of PSMI and PS on Immobilization of Oligonucleotide

Figure 3:
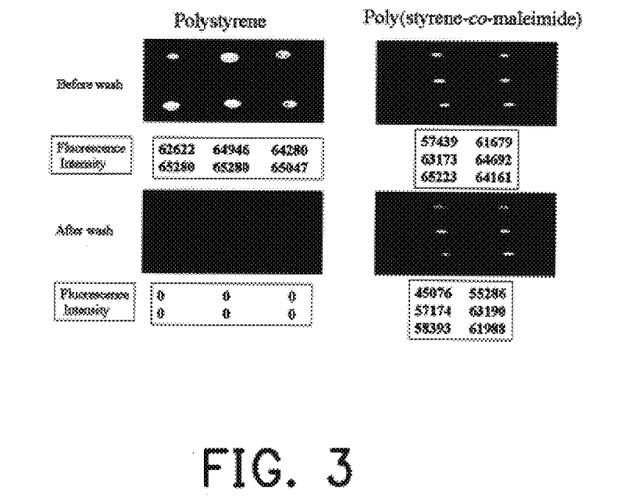
FIG. 3 is a comparative diagram showing the fluorescence intensity after immobilization of labeled oligonucleotide probe using a glass slide coated with PS and PSMI, respectively as a matrix.

PSMI synthesized from Example 1 and PS were coated onto glass substrates, respectively, according to the method described in Example 2. The slides were dried in the oven at 100° C. to remove solvent. A synthetic oligonucleotide probe Sp5 as set forth above was immobilized to the slides to perform a ring-opening reaction. The immobilization conditions were similar to those in Example 2. The fluorescence analyses were performed for the slides with and without washing (control) to monitor the immobilization efficiency. The result is shown in FIG. 3.

EXAMPLE 4

Effect of Acid/Base Treatment on the Surface Hydrophilicity

Figure 4:
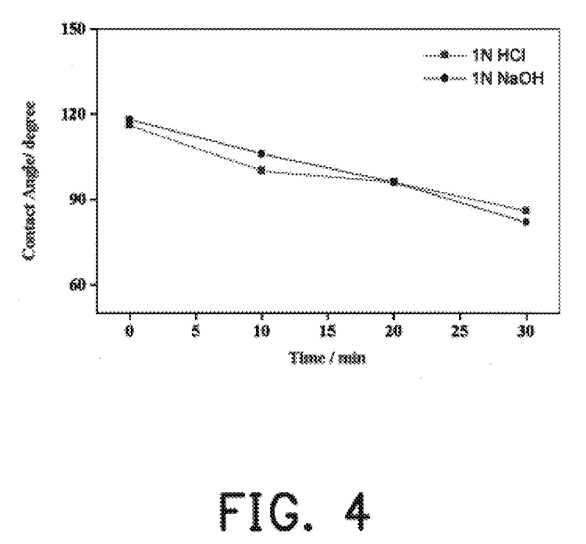
FIG. 4 is a diagram showing changes of contact angle by acid/base solution on the PSMA matrix of the present invention.

PSMA slides prepared from Example 2 were spotted with 1 N HCl and 1 N NaOH, respectively. The contact angle between the droplet and slide was measured at 0, 10, 20, and 30 minutes. The result is shown in FIG. 4.

EXAMPLE 5

Effect of Oligonucleotide Immobilization on the Surface Hydrophilicity

Figure 5:
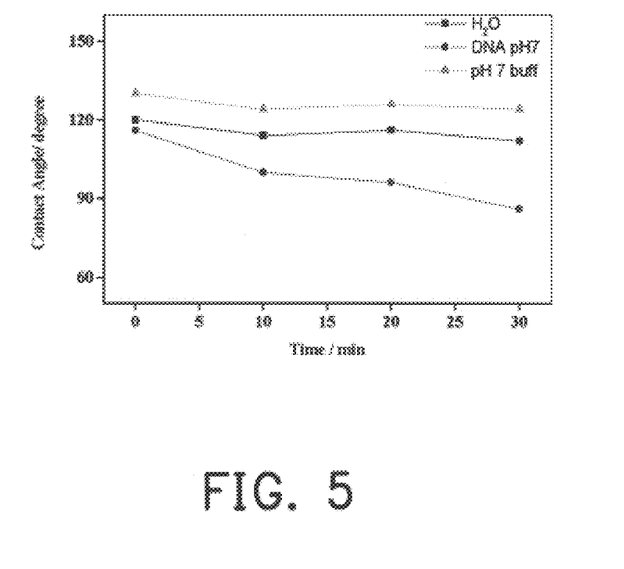
FIG. 5 is a diagram showing in-situ changes of contact angle by water, buffer, or oligonucleotide probe on the PSMA slide of the present invention.

PSMA slides prepared from Example 2 were spotted with de-ionized water, Sp5 probe (pH 7; as set forth above), and buffer (pH 7). The contact angle between the droplet and slide was measured at 0, 10, 20, and 30 minutes. The result is shown in FIG. 5.

EXAMPLE 6

Effect of Various Parameters on Immobilization of Oligonucleotide

Figure 6:
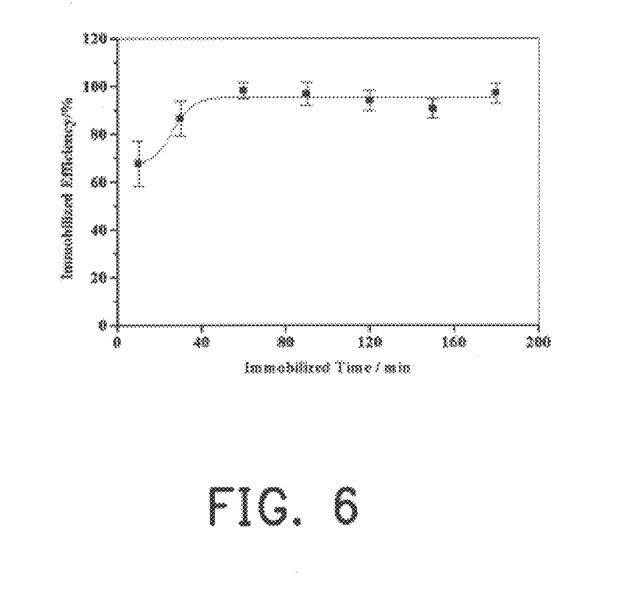
FIG. 6 is a diagram showing the immobilization efficiency of the PSMA matrix of the present invention.
Figure 7:
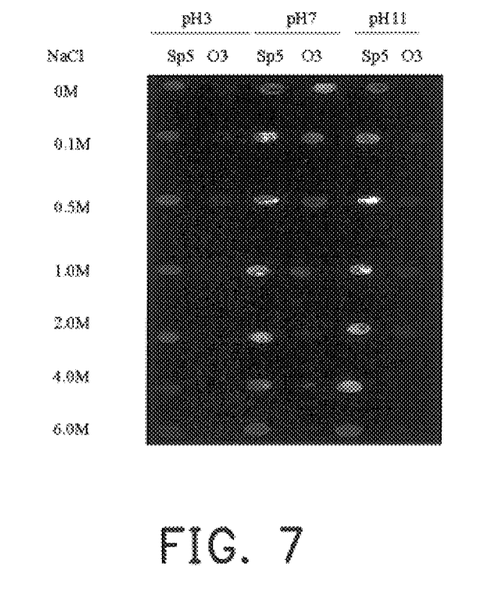
FIG. 7 is a diagram showing the effect of ionic strength and pH on the immobilization of oligonucleotide probe.

PSMA slides were used in this example to test the effect of parameters including time, ionic strength, and pH on the immobilization of oligonucleotide. The immobilization conditions were similar to those in Example 2, wherein the probes used were Sp5 (as set forth above) and $O_3$ (without amine modification at the 5' end). The fluorescence was measured at 10, 30, and 60 minutes to evaluate the relationship of immobilization efficiency with time. In addition, probes were dissolved in 0, 0.1, 0.5, 1.0, 2.0, 4.0, and 6.0 M NaCl solution for immobilization, respectively, to evaluate the relationship between immobilization efficiency and ionic strength. Further, probes were immobilized under the environment of pH 3, pH 7, and pH 11 to evaluate the optimal conditions for immobilization. The results are shown in FIGS. 6 and 7.

EXAMPLE 7

Hybridization with Specific Oligonucleotides

Figure 8:
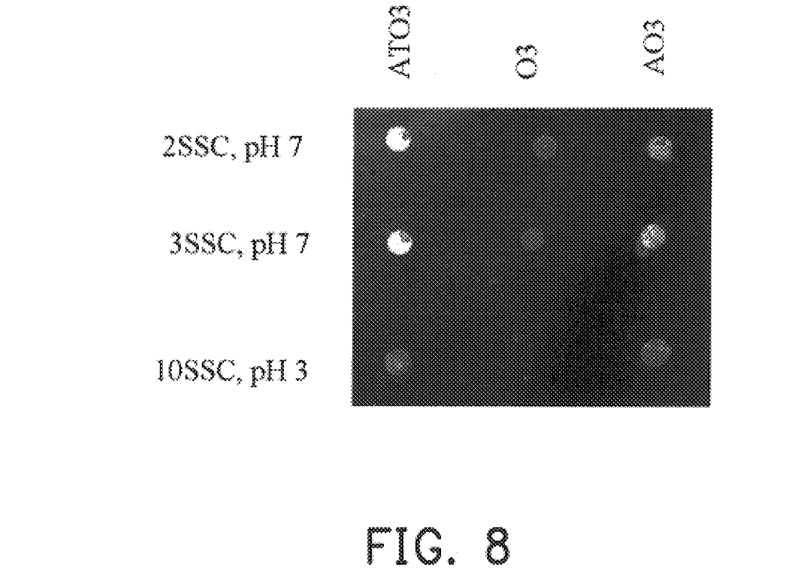
FIG. 8 is a diagram showing the fluorescence intensity after hybridization.

The slides used in this Example were the same as Example 2. The oligonucleotides used in this example were $AO_3$ (composed of 29 nucleotides with amine group at the 5' end); $O_3$ (composed of 29 nucleotides without amine group at the 5' end); and $ATO_3$ (composed of 15 thymidine bases and the same 29 nucleotides as set forth above with amine group at the 5' end), respectively. The probe used for labeling hybridization reaction was the complementary sequence thereto, wherein the 3' end was labeled with fluorescence. The immobilization conditions were 2×SSC, pH 7.0; 3×SSC, pH 7.0; and 10×SSC, pH 3.0, respectively, for 1 hour. The hybridization reaction was performed for 4 hours. The fluorescence was analyzed to monitor the hybridization result. The result is shown in FIG. 8.

EXAMPLE 8

Effect of Organic Slide

Figure 9:
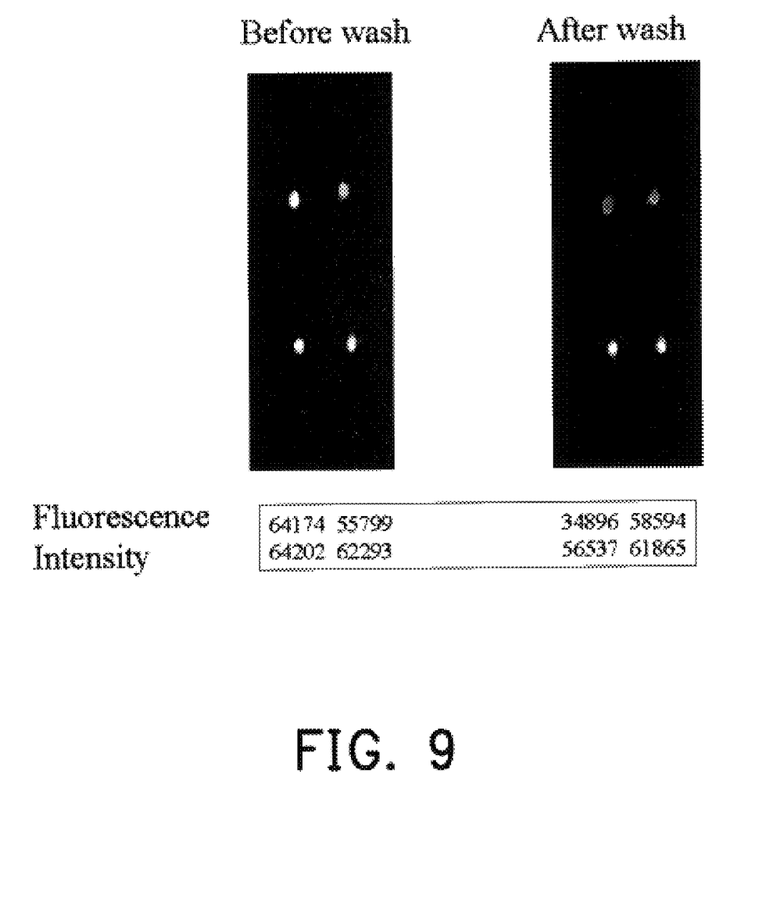
FIG. 9 is a diagram showing the fluorescence intensity using mCOC substrate coated with PSMA as a matrix.

PSMA was coated onto metallocene cycloolefine copolymers (mCOC) substrates at 4,000 rpm. The slides were dried in the oven at 100° C. to remove solvent. A synthetic oligonucleotide probe Sp5 as set forth above was immobilized to the aforementioned slides to perform a ring-opening reaction. The immobilization conditions were similar to those in Example 2. The fluorescence analyses were performed for the slides with and without washing (control) to monitor the immobilization efficiency. The result is shown in FIG. 9.

EXAMPLE 9

Effect of Various Proportions of PSMA on Immobilization of Oligonucleotide

Figure 10A:
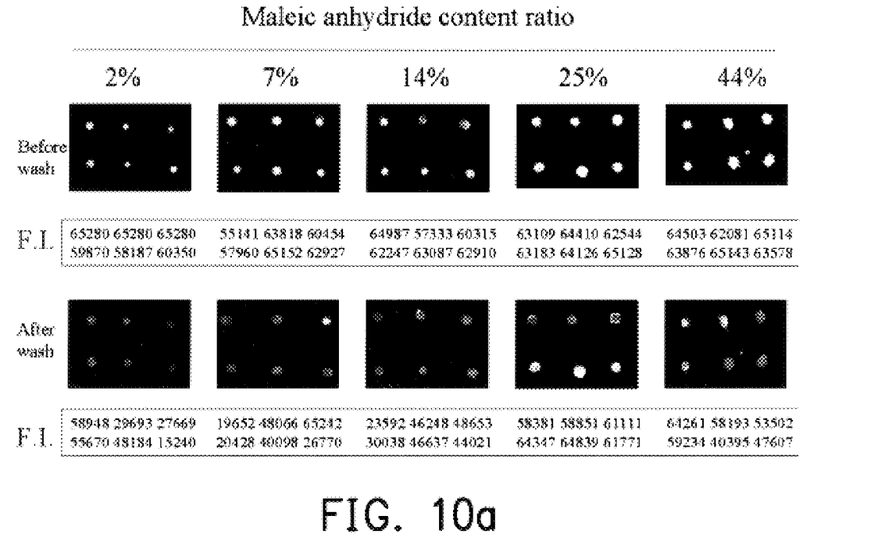
FIG. 10a shows the fluorescence intensity after immobilization of oligonucleotide probe Sp5.
Figure 10B:
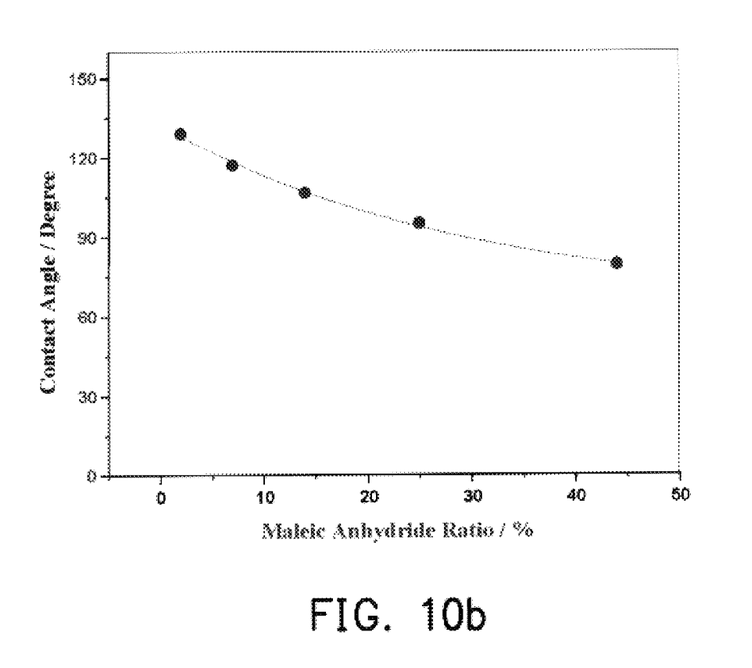
FIG. 10b shows changes of contact angle by water.

PSMA in the range of 2%–44% was coated onto glass substrates, respectively. The coating method and conditions were the same as Example 8 to evaluate the immobilization efficiency of oligonucleotides. The result is shown in FIG. 10a. In addition, de-ionized water was spotted onto the matrices and the contact angle between the droplet and surface of matrix was measured at various composition of PSMA matrices. The result is shown in FIG. 10b.

EXAMPLE 10

RSD Test

Figure 11A:
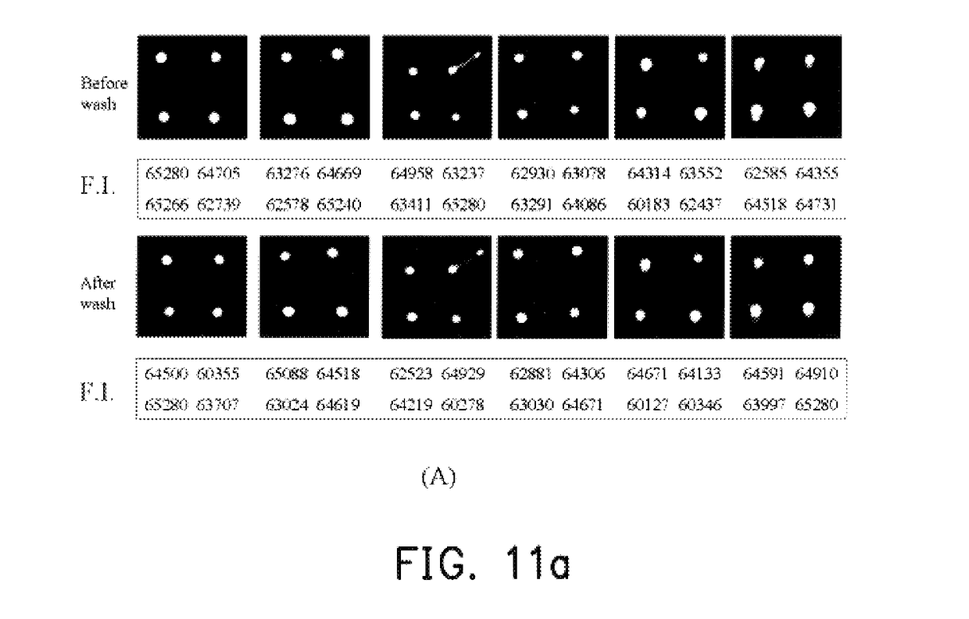
FIG. 11a shows the fluorescence intensity after immobilization of oligonucleotide probe Sp5.
Figure 11B:
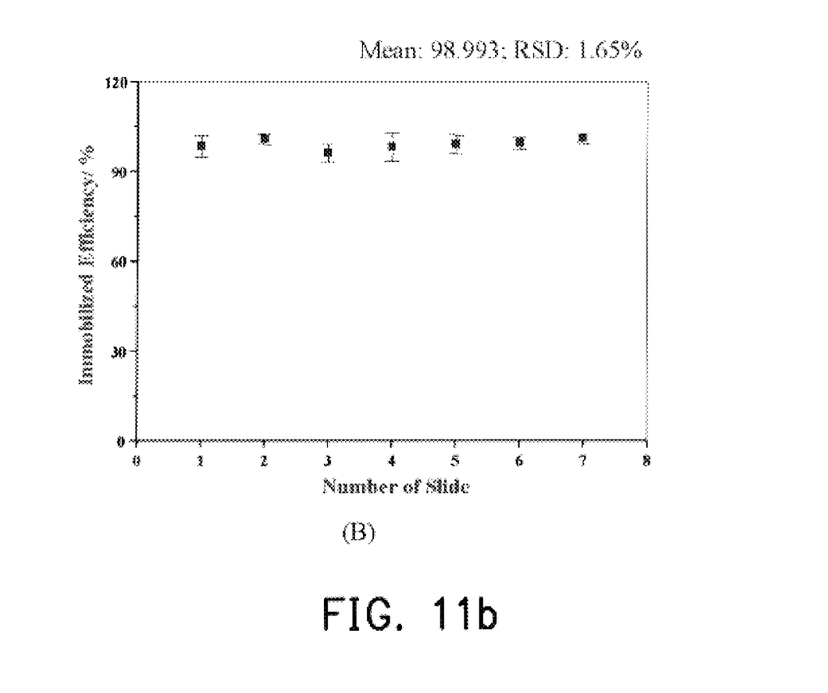
FIG. 11b shows the relative standard deviation (R.S.D.) of the immobilization efficiency.

PSMA slides prepared from Example 2 were used for immobilization of Sp5 probe for 60 minutes under the same conditions. The fluorescence was analyzed for each slide, followed by calculation of the relative standard deviation (R.S.D.) of the immobilization efficiency. The result is shown in FIG. 11.

EXAMPLE 11

Effect of PEMA on Immobilization of Oligonucleotide

Figure 12:
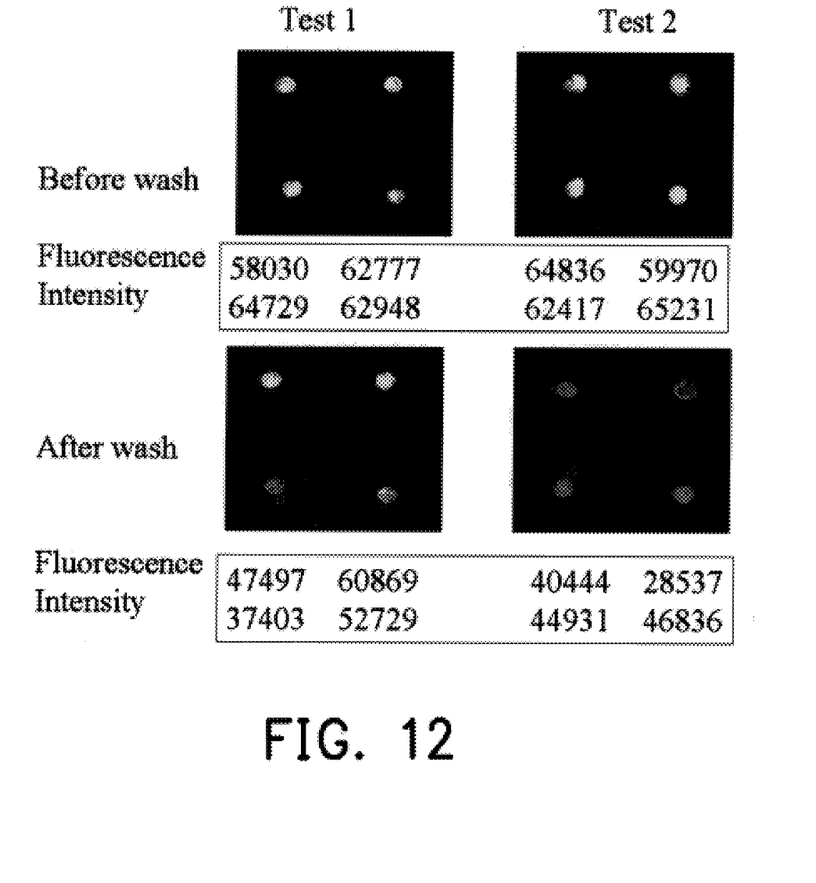
FIG. 12 is a diagram showing the fluorescence intensity using a glass-based matrix coated with PEMA.

PEMA (Aldrich, Cat. No. 43084–6) was coated onto glass substrates according to the method described in Example 2. The slides were dried in the oven at 100° C. to remove solvent. A synthetic oligonucleotide probe Sp5 as set forth above was immobilized to the slides to perform a ring-opening reaction. The immobilization conditions were similar to those in Example 2. The fluorescence analyses were performed for the slides with and without washing (control) to monitor the immobilization efficiency. The result is shown in FIG. 12.

The PSMA, PSMI, and PEMA hydrophobic copolymers of the present invention persist reaction functionalities (e.g. anhydride ring or imide ring) to which the biomaterials can be bonded, so that a bio-molecule such as amine-modified DNA can be stably bonded to the surface of the slides. Referring to FIGS. 2–3, because PS itself cannot provide any functional site for bonding, the oligonucleotide probes were washed out after spotting Sp5 and washing with 0.2% SDS, thus no fluorescent signal can be detected (i.e. biomaterials are not stably adhered to the surfaces). As compared with PSMA or PSMI slides, the Sp5 probe retains at least 90% immobilization efficiency after washing with 0.2% SDS.

Referring to FIG. 4, the contact angle is reduced from 120° to 90° by acid/base treatment on PSMA slide. By contrast, referring to FIG. 5, the contact angle is not reduced markedly by buffer solution(pH 7) and de-ionized water on the slide, indicating there is no hydrophilic conversion occurred thereon, i.e. no ring-opening reaction occurred. After spotting Sp5 probe (pH 7) on the slide, the contact angle is reduced from 120° to 90°, showing the nucleophile (amine) attacks the anhydride ring. This results in ring-opening reaction and bonding between the DNA and slide. Meanwhile, the hydrophilicity is enhanced.

In the conventional method, about 4–16 hours are required for the immobilization of oligonucleotide probe. As shown in FIG. 6, it takes only about 30 minutes for the same effect on the on-spot hydrophilic enhanced slide of the present invention, which is significantly shorter than the prior technique.

Referring to FIG. 7, under the conditions of 0 to 0.1 M ionic strength and pH 7 to 11, the preferred immobilization efficiency is obtained on the on-spot hydrophilic enhanced slide of the present invention.

Referring to FIG. 8, the differences among three probes are that $AO_3$ bears an amine group at the 5' end, whereas $O_3$ is without an amine group. The amine group at the 5' end of $ATO_3$ is ligated with 15 bases of thymidine. Three kinds of probe are immobilized onto the slide at pH 3.0 and 7.0, respectively. From the result of O3 probe, the poor bonding efficiency is observed due to the lack of an amine group at the 5' end. Other probes with amine group at the 5' end possess excellent bonding efficiency. This indicates the specificity of the bonding of the target molecule can be elevated markedly according to the on-spot hydrophilic enhanced slide of the present invention.

FIG. 9 shows the matrix used in the invention is not limited to inorganic substrate. The metallocene cycloolefine copolymer (mCOC) is an organic polymer, and the hydrophobic copolymer of the present invention can be still coated thereon to form a thin layer, which is useful for the subsequent immobilization of biomaterials.

The property of hydrophobicity differs from the proportions of the hydrophobic copolymers, and thus the density of functional groups provided for immobilization is also different. Referring to FIG. 10a, the higher anhydride content, the more hydrophilic is obtained. However, the main chain of the copolymer remains hydrophobic, which is beneficial for the preparation of high-density slides. Meanwhile, referring to FIG. 10b, it is shown that the higher anhydride content, the greater immobilization efficiency obtained. However, the higher hydrophilicity is not suitable for preparing high-density slides. The hydrophobic copolymer containing too much anhydride content is therefore not suitable.

Homogeneity is important for the preparation of microarrays. Referring to FIG. 11, the homogeneity of the hydrophobic copolymer is excellent after coating to the substrate. It shows excellent immobilization efficiency and less than 2% relative standard deviation (R.S.D.).

The component of the hydrophobic copolymer is not limited to styrene/polystyrene. As shown in FIG. 12, the polyethylene (PE) used as the main chain of the copolymer can also develop into an on-spot hydrophilic enhanced slide. Any functionally hydrophobic copolymer containing at least one anhydride, imide, cyclic amide, or cyclic ester can attain the purpose of the present invention.

While the invention has been particularly shown and described with the reference to the preferred embodiment thereof, it will be understood by those skilled in the art that various changes in form and details may be made without departing from the spirit and scope of the invention.

What is claimed is:

1. An on-spot hydrophilic enhanced microarray, comprising.

(i) a substrate;
    (ii) a functionally active layer formed by a hydrophobic copolymer comprising a hydrophobic material and a compound bearing a functional group, wherein said functional group of said compound in said hydrophobic copolymer is at least one selected from the group consisting of anhydride, imide, cyclic amide, and cyclic ester, and wherein said layer is coated onto said substrate; and
    (iii) a biologically active material comprising a nucleophile, wherein said biologically active material is immobilized onto said functionally active layer via a ring-opening reaction between the functional group of the functionally active layer and said nucleophile of said biologically active material.

2. The microarray as claimed in claim 1, wherein the hydrophobic copolymer is prepared by blending, grafting, or co-polymerization of said hydrophobic material with said compound bearing said functional group.

3. The microarray as claimed in claim 2, wherein the hydrophobic material is selected from the group consisting of styrene, urethane, ethylene, and derivatives thereof.

4. The microarray as claimed in claim 3, wherein the hydrophobic copolymer comprises poly(styrene-co-maleic anhydride), poly(styrene-co-maleimide), or poly(ethylene-co-maleic anhydride).

5. The microarray as claimed in claim 1, wherein the substrate comprises organic or inorganic substrate.

6. The microarray as claimed in claim 5, wherein the organic substrate comprises a polymer polymerized by organic monomers, wherein said organic monomers is selected from the group consisting of a monomer of ethylene, styrene, propylene, ester, acrylic acid, acrylate, alkyl acrylic acid, and alkyl acrylate.

7. The microarray as claimed in claim 6, wherein the organic substrate comprises substrate consisting of poly (styrene-co-maleic anhydride), poly(styrene-co-maleimide), or poly(ethylene-co-maleic anhydride).

8. The microarray as claimed in claim 5, wherein the inorganic substrate comprises silicon wafer, ceramic material, glass, or metal.

9. The microarray as claimed in claim 1, wherein the biologically active material comprises nucleic acid, peptide, peptide nucleic acid, antigen, antibody, enzyme, or protein.

10. The microarray as claimed in claim 1, wherein said microarray is characterized by the on-spot hydrophilic enhancement when the use of immobilization of the biologically active materials.

11. The microarray according to claim 1, wherein the biologically active material is an oligonucleotide.

12. The microarray according to claim 1, wherein said nucleophile of said biologically active material is an amine or amino group.

* * * * *

UNITED STATES PATENT AND TRADEMARK OFFICE
CERTIFICATE OF CORRECTION

PATENT NO. : 6,403,368 B1
DATED : June 11, 2002
INVENTOR(S) : Bor-Iuan Jan et al.

It is certified that error appears in the above-identified patent and that said Letters Patent is hereby corrected as shown below:

<u>Title page,</u>
Item [75], Inventor, fourth inventor is missing and should be:
-- Yu-Ching Liu, Taichung Hsien; --

Signed and Sealed this

Twenty-second Day of October, 2002

Attest:

Attesting Officer

JAMES E. ROGAN
*Director of the United States Patent and Trademark Office*